United States Patent [19]

Yokokawa et al.

[11] Patent Number: 5,266,596
[45] Date of Patent: Nov. 30, 1993

[54] L- OR DL-THREO-3-(3,4-DIHYDROXYPHENYL)SERINE FOR THE TREATMENT OF URINARY INCONTINENCE

[75] Inventors: Kiyoshi Yokokawa, Nishinomiya; Shuji Takaori, Izumo, both of Japan

[73] Assignee: Sumitomo Pharmaceuticals Co., Ltd., Osaka, Japan

[21] Appl. No.: 858,184

[22] Filed: Mar. 26, 1992

[30] Foreign Application Priority Data

Mar. 27, 1991 [JP] Japan .................................. 3-089766

[51] Int. Cl.$^5$ ........................................... A61K 31/195
[52] U.S. Cl. ..................................... 514/567; 514/869
[58] Field of Search .......................... 514/555, 567, 869

[56] References Cited

U.S. PATENT DOCUMENTS 4,647,587  3/1989  Katsube et al. ...................... 514/567

FOREIGN PATENT DOCUMENTS 0177356  4/1986  European Pat. Off. .

OTHER PUBLICATIONS

Urology, vol. 5, No. 5, 1975, pp. 624–625; A. C. Diokno et al.: "Ephedrine in Treatment of Urinary Incontinence".

Scandinavian Journal of Urology and Nephrology, vol. 12, No. 2, 1978, pp. 105–110; K. E. Andersson et al "The Effects of Long-Term Treatment with Norephedrine on Stress Incontinence and Urethral Closure Pressure Profile".

The Japanese Journal of Pharmacology, vol. 52, No. 3, Mar., 1990; pp. 431–439; S. Morimoto et al, "Diuretic Effects of L-Threo-3,4-Dihydroxyphenylserine in Anesthetized Rats".

STN File Supplier, Medline AN-89280494, 1989, and Nippon Hinyokika Gakkai Zasshi vol. 80, No. 3, 1989 Japan pp. 416–423; Morita T.: 'Experiment Studies on Urinary Incontinence'.

PH. Dorosz "Guide Pratique Des Medicaments" 1987, Maloine S. A. Editeur, Paris pp. 848–849.

Scandinavian Journal of Urology and Nephrology, vol. 17, No. 3, 1983, pp. 261–265; K. E. Andersson et al: "The Effect of Mododrine and Its Active Metabolite ST 1059 on the Human Urethra In Vitro and In Vivo".

Hayashi et al, "Effect of Oral L-threo-3,4-dihydroxyphenylserine on Patients with Severe Orthostatic Hypotention Secondary to Autonomic Neuropathy," The Journal of the Japan Diabetes Society, vol. 29, No. S1, 1986.

J. E. F. Reynolds 'Martindale, The Extra Pharmacopoeia' 1989, The Pharmaceutical Press, London "DL--Threo-3,4-Dihydroxyphenylserine", p. 1564.

The Lancet, 1987, pp. 1170–1172, I. Biaggioni et al: "Endogenous Restoration of Noradrenaline by Precursor Therapy in Dopamine-Beta-Hydroxylase Deficiency".

N. Yoshimura et al, "Contraction of Urinary Bladder by Central . . . the Locus Coeruleus", The Journal of Urology, vol. 139, Feb., 1988, pp. 423–427.

R. Freeman et al, "The Treatment of Orthostatic Hypotension with Dihydroxyphenylserine", Clinical Neuropharmacology, vol. 14, No. 4, 1991, pp. 296–304.

N. Yoshimura et al, "Mediation of Micturition Reflex . . . Coeruleus in the Cat", The Journal of Urology, vol. 143, Apr., 1990, pp. 840–843.

Primary Examiner—Frederick E. Waddell
Assistant Examiner—T. J. Criares
Attorney, Agent, or Firm—Sughrue, Mion, Zinn, Macpeak & Seas

[57] ABSTRACT

DL- or L-threo-3-(3,4-dihydroxyphenyl)serine is effective for the treatment of urinary incontinence, shows no side effects such as urine discharge disturbance, palpitation and hypertension, and has low toxicity.

2 Claims, No Drawings

L- OR DL-THREO-3-(3,4-DIHYDROXYPHENYL)SERINE FOR THE TREATMENT OF URINARY INCONTINENCE

BACKGROUND OF THE INVENTION

1. Field of the Invention

The present invention relates to a pharmaceutical composition for the treatment of urinary incontinence comprising DL- or L-threo-3-(3,4-dihydroxyphenyl)serine or a pharmaceutically acceptable acid addition salt thereof as an active ingredient.

2. Statement of Related Art

In the U.S.A., urinary incontinence, dementia and osteoporosis have been considered especially serious diseases for the aged people, and therapeutics therefor have become a medical and social problem awaiting prompt solution. Likewise in Japan, attention has been similarly brought to new medical problems for the aged people. Therefore, therapeutics for the aged people is desired to maintain and improve the quality of life in old age. In particular, urinary incontinence is a typical disease that deteriorates the quality of life of the aged people. Not only for the patients but also for their family, urinary incontinence is a serious burden. However, the patients usually feel ashamed of consulting about the urinary incontinence. In addition, therapeutics for urinary incontinence has not been extensively developed, because it would not be a fatal disease. Accordingly, only a few medicines for the treatment of urinary incontinence have been clinically used. For example, an anticholinergic agent, an α-receptor stimulator, an antidepressant, an estrogen, an autonomic nerve function modulator and a minor tranquillizer have been clinically used hitherto.

However, the anti-cholinergic agents and Imipramine which have been conventionally used have side effects such as thirst, constipation and nasal obstruction, and hence, their applications often accompany undesirable difficulties. In particular, an excessive anti-cholinergic activity causes micturition disturbance that is considered undesirable to the treatment of urinary incontinence.

After all, the more effective a medicine is in a principal action, the more serious it generally shows side effects. These side effects in many cases cause discomfort with the patients and fail to improve their quality of life.

Since most outpatients who suffer from urinary incontinence can spend their every-day life not much different from healthy people, it has been highly desired to develop an effective medicine for the treatment of urinary incontinence without side effects.

SUMMARY OF THE INVENTION

As a result of extensive investigations, the present inventors have found that DL- or L-threo-3-(3,4-dihydroxyphenyl)serine exhibits an excellent effect in the treatment of urinary incontinence.

That is, the present invention relates to a pharmaceutical composition for the treatment of urinary incontinence comprising as an active ingredient DL- or L-threo-3-(3,4-dihydroxyphenyl)serine or a pharmaceutically acceptable acid addition salt thereof.

According to one aspect of the present invention, there is provided a method for the treatment of urinary incontinence which comprises administering to a human body DL- or L-threo-3-(3,4-dihydroxyphenyl)serine or a pharmaceutically acceptable acid addition salt thereof in a pharmaceutically effective amount.

According to another aspect of the present invention, there is provided use of DL- or L-threo-3-(3,4-dihydroxyphenyl)serine or a pharmaceutically acceptable acid addition salt thereof for the preparation of a pharmaceutical composition for the treatment of urinary incontinence.

DETAILED DESCRIPTION OF PREFERRED EMBODIMENTS

DL- or L-threo-3-(3,4-dihydroxyphenyl)serine (hereinafter abbreviated as DL- or L-threo-DOPS) used in the present invention is a known compound and can be prepared, for example, by a method as described in Japanese Patent Application KOKOKU No. 1-49139.

DOPS is classified into the threo form (threo-DOPS) and the erythro form (erythro-DOPS) depending on the steric configuration. Each of those forms has further optical isomers. Thus, DOPS has 4 steric isomers, i.e., L-threo-DOPS, D-threo-DOPS, L-erythro-DOPS and D-erythro-DOPS.

Among them, only L-threo-DOPS is already known to undergo decarboxylation by the action of aromatic L-amino acid decarboxylase to produce natural l-noradrenaline (hereafter referred to as l-NA). On the other hand, as for the pharmacological activities of L-threo-DOPS, there are many reports on the sympathomimetic activities such as an inhibitory action on Harmalin-induced tremor and pressure activity on blood pressure. Based on these pharmacological activities, L-threo-DOPS has been provided for clinical use since 1989, as a medicine for intractable diseases such as orthostatic hypotension and freezing symptoms in Parkinson's disease.

In the present invention, "urinary incontinence" is used to mean that bladder urine leaks involuntarily from the urethra due to the failure of the continence mechanism.

While the reaction mechanism of DL- or L-threo-DOPS in the present invention is now under investigations, it is supposed that there would be a possibility for DL- or L-threo-DOPS to exhibit its activity based on l-NA, because many pharmacological activities of L-threo-DOPS are diminished when the conversion of L-threo-DOPS into l-NA is inhibited. Several studies on the pharmacological activities of l-NA on the kidney function, urinary bladder and urethra have been reported heretofore. However, the anti-urinary incontinence activity of DL- or L-threo-DOPS according to the present invention has not been anticipated by these reports.

Urinary incontinence is noted in women with fragile pelvic muscles, patients with central nervous lesion such as cerebro-vascular disorder sequela or spinal injury, patients with cystitis or prostatic hypertrophy, and in addition the aged people or patients with dementia. As causes of urinary incontinence, there may be suspected various factors such as disorders in muscular function around the pelvis, functional disturbance of urinary bladder or urethral smooth muscle and disorders in peripheral or central nervous systems.

It is known that in the autonomic nervous system in the lower urethra, sympathetic nerve relaxes the urinary bladder detrusor muscle via β-receptor and contracts the urinary bladder neck and urethra via α-receptor. On the other hand, it has been revealed by physiological and pharmacological researches that the central 1-NA nerve system (from nucleus *Loci caerulei*) centrally regulates the urine discharging mechanism via parasympathetic nerve system in the sacral region of from spinal cord to the urinary bladder. It is considered that due to regulation mechanisms of this central 1-NA nerve, one could perform the urine discharging motion by one's own will. If the central 1-NA nerve function is hindered, urine would be involuntarily leaked out when urine is retained in the urinary bladder in a certain volume, resulting in urinary incontinence.

Considering the above, it might be postulated that 1-NA as a sympathetic nerve neurotransmitter would be effective for urinary incontinence. However, no attempt to use 1-NA for urinary incontinence has been reported hitherto. In addition, it may be difficult to clinically use 1-NA, because immediately after injection, 1-NA exerts drastic effects on circulating system to cause hypertension and palpitation, and its duration is shorter, rather instantaneous. Furthermore, when administered to the peripheral, 1-NA may not be expected to act centrally, because 1-NA lacks transferability to the brain. On the other hand, after administered, DL- or L-threo-DOPS is distributed both centrally and peripherally and then gradually converted into 1-NA to act moderately. Accordingly, the effect of DL- or L-threo-DOPS on urinary incontinence according to the present invention is based on the excellent property as a prodrug for 1-NA. The effect of DL- or L-threo-DOPS should not be merely conceived from the conventional pharmacological activity of 1-NA.

In the present invention, DL- or L-threo-DOPS may be used in the form of pharmaceutically acceptable acid addition salts, too. Inorganic acids such as hydrochloric acid, hydrobromic acid and sulfuric acid; and organic acids such as fumaric acid, citric acid, tartaric acid and succinic acid may be used as acids for forming the acid addition salts.

L-Threo-DOPS or pharmaceutically acceptable acid addition salts thereof may be orally or parenterally administered at a dose depending on individual recipients in a conventional dosage form. For example, they may be administered orally in the form of a tablet, a capsule, syrup or a suspension, or parenterally in the form of an injection such as a solution, an emulsion and a suspension.

The preparation as described above may be prepared by conventionally formulating the active ingredient together with conventional carriers, excipients, binders or stabilizers. Where the active ingredient is formulated to an injection, a buffer, a dissolution aid or an isotonic agent, which are conventionally used, may also be added.

Dose of the active ingredient and the number of administrations vary depending upon how to administrate and condition of disease to be treated, but in the case of, e.g., oral administration, at a dose in the range of 0.1 to 3 g per day the active ingredient is administered to adult once or by dividing the dose into several times.

The toxicity of the active ingredient is extremely low. $LD_{50}$ in mouse is 10 g/kg or more at oral administration route and about 10 g/kg at intraperitoneal administration route. In view of these values, the effective dose as indicated hereinbefore are considered not to be harmful.

EXAMPLE

Hereafter, the clinical effect is discussed in more detail based on the following clinical test results.

Recipients and Methods

L-Threo-DOPS was administered (100 mg×3 times, a 4 weeks) to 13 patients with urinary incontinence in the clinic of urology. For estimating the effect on urinary incontinence and side effects, the patients were investigated medically before and after the treatment with L-Threo-Dops. The patients were 6 males and 7 females in the range of 35 to 76 years old, and were 51.8 years old in average. Further, by urodynamic study, the patients were classified into urgent urinary incontinence (7 patients), stress urinary incontinence (3 patients) and other condition (3 patients).

Results

The clinical results of patents with treatment of L-threo-DOPS are shown in Tables 1 to 4.

In 10 out of 13 cases, the clinical effect of more than a slight improvement was noted. Disappearance of the symptoms or improvement to a moderate degree or more was noted in 9 cases in total, i.e., 5 out of 7 cases with urgent urinary incontinence, 2 out of 3 cases with stress urinary incontinence and 2 out of 3 other cases. L-threo-DOPS was almost ineffective in the remaining 4 cases. In all cases, however, side effects such as urine discharge disturbance, palpitation and hypertension were not noted and the patients improved felt highly satisfactory. In some cases, the inner pressure of the urinary bladder and urethra was measured before and after administration of L-threo-DOPS, whereby an increased volume of the urinary bladder was confirmed.

TABLE 1

| | Clinical Effect | | | |
|---|---|---|---|---|
| Case No. | 1 | 2 | 3 | 4 |
| Sex | Male | Male | Female | Female |
| Age (year) | 67 | 76 | 42 | 51 |
| Main condition | Urgent urinary incontinence | Urgent urinary incontinence Pollakiuria | Urgent urinary incontinence | Urgent urinary incontinence |
| Complication | Lumbago deformans Hypertension | None | None | None |
| Dose (dose × week) | 300 mg/ day × 4 weeks | 300 mg/ day × 4 weeks | 300 mg/ day × 4 weeks | 300 mg/ day × 4 weeks |
| Clinical effect | Markedly improved | Markedly improved | Markedly improved | Markedly improved |
| Side effect | None | None | None | None |

TABLE 2

| | Clinical Effect | | | |
|---|---|---|---|---|
| Case No. | 5 | 6 | 7 | 8 |
| Sex | Male | Female | Female | Female |
| Age (year) | 52 | 64 | 42 | 51 |
| Main condition | Enuresis nocturna Disuria | Stress incontinence | Urgent urinary incontinence | Stress incontinence |
| Complication | Gait disturbance Disturbance of memorizing Hernia of intervertebral disk | None | None | Hypertension |
| Dose (dose × | 300 mg (3) × 4 weeks | 300 mg (3) × | 300 mg (3) × | 300 mg (3) × 4 weeks |

TABLE 2-continued

| | Clinical Effect | | | |
|---|---|---|---|---|
| Case No. | 5 | 6 | 7 | 8 |
| week) | | 4 weeks | 4 weeks | |
| Clinical effect | Slightly improved | Not effective | improved | improved |
| Side effect | None | None | None | None |

TABLE 3

| | Clinical Effect | | | |
|---|---|---|---|---|
| Case No. | 9 | 10 | 11 | 12 |
| Sex | Female | Female | Male | Male |
| Age (year) | 49 | 51 | 36 | 42 |
| Main condition | Stress incontinence | Overflow incontinence | Urgent urinary incontinence | Urgent urinary incontinence |
| Complication | None | None | Pollakiuria | Enuresis nocturna |
| Dose (dose × week) | 300 mg/day × 4 weeks | 300 mg/day × 4 weeks | 300 mg/day × 4 weeks | 300 mg/day × 4 weeks |
| Clinical effect | Improved | Not effective | Markedly improved | Not effective |
| Side effect | None | None | None | None |

TABLE 4

| | Clinical Effect |
|---|---|
| Case No. | 13 |
| Sex | Male |
| Age (year) | 35 |
| Main condition | Enuresis |
| Complication | Mentally handicapped |
| Dose (dose × week) | 300 mg/day × 4 weeks |
| Clinical effect | Improved |
| Side effect | None |

As stated above, DL- or L-threo-DOPS according to the present invention showed an excellent effect on urinary incontinence. It had been theoretically predicted that the active ingredient of the present invention might cause urine discharge disturbance when urinary incontinence disappeared, as observed in other conventional medicines. However, in all of the cases, no side effects were noted, even tendency of dysuria was not noted, either.

Therefore, according to the present invention there is provided for the first time an excellent pharmaceutical composition for the treatment of urinary incontinence without side effects, which has been long desired.

What is claimed is:

1. A method for the treatment of urinary incontinence which comprises administering to a human body DL- or L-threo-3-(3,4-dihydroxyphenyl)serine or a pharmaceutically acceptable acid addition salt thereof in a pharmaceutically effective amount.

2. A method according to claim 1, wherein L-threo-3-(3,4-dihydroxyphenyl)serine or a pharmaceutically acceptable acid addition salt thereof is administered.

* * * * *